United States Patent [19]

Massaroli

[11] 4,254,126

[45] Mar. 3, 1981

[54] 4-CARBETHOXY-CARBONILAMINO-PYRIMIDINES AND A PROCESS FOR THEIR PREPARATION

[75] Inventor: Giangiacomo Massaroli, Milan, Italy

[73] Assignee: POLI Industria Chimica S.p.A., Milan, Italy

[21] Appl. No.: 87,066

[22] Filed: Oct. 22, 1979

[30] Foreign Application Priority Data

Dec. 18, 1978 [IT] Italy ................................ 30943 A/78

[51] Int. Cl.³ .................. A61K 31/505; C07D 239/34
[52] U.S. Cl. .................................... 424/251; 544/317; 544/319; 544/329; 544/312
[58] Field of Search ............... 544/312, 317, 319, 329, 544/251

Primary Examiner—Donald G. Daus
Assistant Examiner—James H. Turnipseed
Attorney, Agent, or Firm—Michael J. Striker

[57] ABSTRACT

New compounds, carbethoxy-carbonilamino pyrimidines are prepared from 4-amino pyrimidines and find application in pharmaceutical compositions for the treatment of allergic reactions and peptic ulcer.

19 Claims, No Drawings

4-CARBETHOXY-CARBONILAMINO-PYRIMIDINES AND A PROCESS FOR THEIR PREPARATION

DESCRIPTION

The present invention relates to new compounds, carbethoxy-carbonilamino-pyrimidines of the general formula (I)

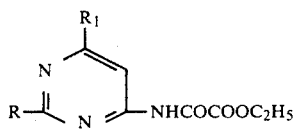
(I)

in which
R=H, CH$_3$, C$_6$H$_5$, SCH$_3$
R$_1$=H, Cl, OCH$_3$, OCH$_2$CH$_2$OCH$_3$, SCH$_2$CH$_2$CH$_2$COOC$_2$H$_5$, SCH$_3$, SCH$_2$CH$_2$OH, SCH$_2$CH$_2$OCOCOOC$_2$H$_5$, OCH$_2$CH$_2$OCH$_2$C$_6$H$_5$, SCH$_2$CH$_2$OCH$_3$, SCH$_2$CH$_2$OCH$_2$CH$_2$OCH$_3$ and a method for their preparation and to pharmaceutical compositions containing compounds of the general formula (I) effective against allergic reactions and gastric ulcers.

The invention also relates to new compounds intermediate in the preparation of compounds of the general formula (I).

In accordance with the invention, the compounds of the general formula (I) are obtained through reaction of compounds of a general formula (II)

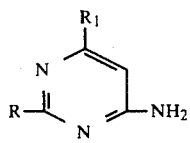
(II)

in which R and R$_1$ have the significances as shown above, with ethoxallyl chloride in the presence of a suitable acceptor of hydrochloric acid, such as for instance pyridine or N,N-dimethyl aniline in a non-polar solvent, or with a stoichiometric excess of diethyl oxalate at the boiling point of the reaction mixture.

The intermediaries of the general formula (II) will in some cases be already known in the literature. The intermediaries (II) in which R$_1$ represents OCH$_2$CH$_2$OCH$_3$,

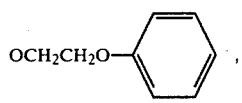

OCH$_2$CH$_2$OCH$_2$CH$_2$OCH$_3$, not previously known in the literature, are prepared through reaction of a compound of the general formula (III)

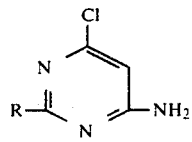
(III)

in which R has the significances quoted above, with a compound of the general formula (IV)

R$_1$-Me   (IV)

where R$_1$ represents precisely one of the groups OCH$_2$CH$_2$OCH$_3$,

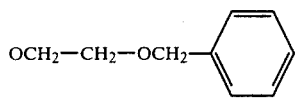

OCH$_2$CH$_2$OCH$_2$CH$_2$OCH$_3$, while Me represents an alkaline metal, preferably sodium.

It is likewise possible to prepare the compounds (II) in which R$_1$ represents OCH$_2$CH$_2$OCH$_3$,

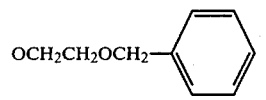

OCH$_2$CH$_2$OCH$_2$CH$_2$OCH$_3$ through the heating of a compound of formula (III) with a surplus of a compound of formula (V) where R$_1$ represents precisely one of the groups OCH$_2$CH$_2$OCH$_3$,

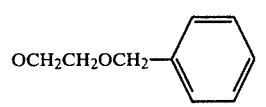

OCH$_2$CH$_2$OCH$_2$CH$_2$OCH$_3$, in the presence of sodium or potassium carbonate.

The intermediaries (II) in which R$_1$ represents SCH$_2$CH$_2$CH$_2$COOC$_2$H$_5$, SCH$_2$CH$_2$OH, SCH$_2$CH$_2$OCH$_3$, SCH$_2$CH$_2$OCH$_2$CH$_2$OCH$_3$ are prepared from compounds (III) by means of reaction with KSH to give the compounds of formula (VI)

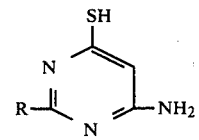
(VI)

(where R has the significances stated above) which are in their turn caused to react with compounds of a general formula (VII)

R$_2$X   (VII)

in which R$_2$ represents CH$_2$CH$_2$CH$_2$COOC$_2$H$_5$, CH$_2$CH$_2$OH, CH$_2$CH$_2$OCH$_3$, CH$_2$CH$_2$OCH$_2$CH$_2$OCH$_3$ and X represents a halogen or the group

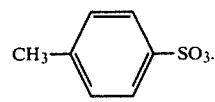

The following examples illustrate the invention clearly, without nevertheless restricting it. The structure of the intermediaries and of the final products has been confirmed both by component analysis and by IR and NMR spectra.

EXAMPLE 1

4-amino-6-β-methoxyethoxy-pyrimidine (II, with R=H; $R_1$=OCH$_2$CH$_2$OCH$_3$)

11.5 g of sodium (0.5 g atoms) are dissolved in 375 ml of methyl cellosolve solvent. 65 g of 4-amino-6-chloropyrimidine (0.5 mol) are added to the solution and the reaction mixture is heated for four hours at 100° C. The excess of the methyl cellosolvesolvent is evaporated in a vacuum and the residue is recovered with 200 ml of water. The solution is saturated with potassium carbonate and is extracted with ethyl acetate.

The extracts are evaporated in a vacuum and the solid residue is crystallised from ethyl acetate plus petroleum ether. 67 g of product is obtained (80% yield) with a melting point 114°–16° C.

Note—the reaction can be carried out with the same results replacing the metallic sodium with potassium carbonate (104 g for 0.5 mol of 4-amino-6-chloropyrimidine).

EXAMPLE 2

4-amino-6-β-methoxyethylthio-pyrimidine (II, with R=H; $R_1$=SCH$_2$CH$_2$OCH$_3$)

20 g of sodium hydroxide (0.5 mol) are dissolved in 500 ml of ethanol/water at 1:1. 63.5 g of 4-amino-6-mercaptopyrimidine (0.5 mol) are added to the solution and the temperature of the solution is brought to 60° C. 115 g of p-toluene sulphonate of β-methoxyethyl (0.5 mol) are added drop by drop over 30 minutes, maintaining the temperature at 60° C. with a water bath. The addition terminated, the reaction mixture is refluxed for three hours. Then the solvent is evaporated and the residue is recovered with 250 ml of water. The aqueous solution is repeatedly extracted with chloroform (6×100 ml) and the amalgamated extracts are evaporated until dry. The solid residue is crystallised from ethyl acetate plus petroleum ether. 74 g of product are obtained (80% yield) with a melting point of 78°–80° C.

In Table 1 the physico-chemical characteristics are listed of the compounds of general formula (II) not known in the literature, prepared according to the procedure described in Examples 1 and 2.

TABLE 1

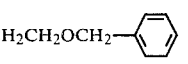
(II)

| R | $R_1$ | Melting Point - °C. |
|---|---|---|
| C$_6$H$_5$ | OCH$_3$ | 115–116 |
| CH$_3$ | OCH$_2$CH$_2$OCH$_3$ | 94–96 |
| CH$_3$ | OCH$_2$CH$_2$OCH$_2$—⟨ ⟩ | 97 |
| CH$_3$ | SCH$_3$ | 140–142 |
| CH$_3$ | SCH$_2$CH$_2$OH | 159–161 |
| H | OCH$_2$CH$_2$OCH$_3$ | 114–116 |
| H | SCH$_2$CH$_2$CH$_2$COOC$_2$H$_5$ | 81–82 |
| CH$_3$ | SCH$_2$CH$_2$OCH$_3$ | 118–122 |
| H | OCH$_2$CH$_2$OCH$_2$CH$_2$OCH$_3$ | 128–130 |
| H | SCH$_2$CH$_2$OCH$_2$CH$_2$OCH$_3$ | 65–66 |

EXAMPLE 3

4-carbethoxycarbonilamino-6-(β-methoxyethoxy)-pyrimidine (I, with R=H; $R_1$=OCH$_2$CH$_2$OCH$_3$)

85 g of 4-amino-6-β-methoxy-ethoxy pyrimidine (0.5 mol) are dissolved in 300 ml of anhydrous pyridine. 82 g of ethoxalyl chloride (0.6 mol) are added drop by drop and while stirring at a temperature of 0° C. The addition terminated heating is carried out at 40° C. for two hours.

The surplus pyridine is evaporated under a vacuum and the residue is recovered with H$_2$O. The solid is filtered, is crystallised from ethyl alcohol and the product is dried at 40° C. under a vacuum. 107 g of product are obtained (80% yield) with a melting point of 88°–9° C.

All the other compounds listed in Table 2 are obtained with a similar procedure.

The compounds of general formula (I) are all endowed with an extremely low toxicity (the DL$_{50}$ per os in rats is higher than 1600 mg/kg for all the compounds) and they are rapidly absorbed through oral administration, so that the DE$_{50}$ (the dosage capable of reducing the effects of the noxious stimulus by 50%) in the Passive Cutaneous Anaphylaxis Test in the rat is almost the same whether administered orally or intraperitoneally.

The evaluation of the biological activity of the compounds in accordance with the present invention is described in detail later.

Passive Cutaneous Anaphylaxis (PCA test) in the Rat (a) Production of antiovalbumin reaginic serum. Male rats (COBS-CD) weighing 300 to 400 g, are immunized by intramuscular injection of 0.1 ml/kg of ovalbumin solution obtained by dissolving 20 mg of ovalbumin (Sigma) in 1 ml of saline and by intraperitoneal injection of 1 ml of pertussis vaccine (Abetin Sclavo). After eleven days the animals are killed, the blood collected and after one night at 4° C., centrifuged and sera stored at −20° C.

(b) PCA test—Male rats (COBS-CD) weighing 125 to 135 g were sensitized by two intradermal injections on the shaved back of 0.1 ml of anti-ovalbumin serum. After 24 hours, 25 mg/kg of ovalbumin and 25 mg/kg of Evans blue are injected intravenously and thirty minutes later the animals are killed, the skin of the back removed and the major and minor diameters of the two spots on the reflected skin are measured. The activity of the compounds administered 5 minutes before the antigen are expressed in Table 2 as ED$_{50}$ (the dose which reduces by 50% the average of the diameters of the two spots as compared to controls).

The pharmacological study of the antiulcer activity of the compounds, in accordance with the present invention, has been carried out determining the dose which inhibits the gastric acid secretion by 50% (ED$_{50}$) in pylorus ligated rats (Shay rats) according to the method described by Shay et al., in Gastroenterology 26, 906, 1954, the dose which reduces by 50% (ED$_{50}$) the indomethacin-induced ulcers according to the procedure described by Leet et al., in Arch. Int. Pharmacodyn. 191, 370, 1971 and the dose which reduces by 50% (ED$_{50}$) the ulcers by cold and restraint according to the procedure described by Senay and Levine in Proc. Soc. Exp. Biol. Med. 124, 1221, 1967. The results are shown in Table 2.

The compounds in accordance with the present invention are particularly interesting for use in human therapy for the prevention and treatment of asthma and other types of allergic diseases.

The said compounds can be employed in the form of tablets or capsules or in any other form which allows an oral administration to patients of any age and sex.

For example hard gelatine capsules are given containing 20 to 100 mg of the active principle, 100 mg of lactose and 2 mg of magnesium stearate, or capsules containing 20 to 100 mg of the active principle, 200 mg of starch and 5 mg of talc.

The proposed daily dosage can vary between 50 and 100 mg.

It is also possible to administer the compounds of the present invention parenterally or in aerosol form.

3. 4-carbethoxy-carbonilamino-6-methoxy-pyrimidine.
4. 4-carbethoxy-carbonilamino-2-phenyl-6-methoxy-pyrimidine.
5. 4-carbethoxy-carbonilamino-2-methyl-6-methoxy-pyrimidine.
6. 4-carbethoxy-carbonilamino-2-methyl-6-($\beta$-methoxy-ethoxy)-pyrimidine.
7. 4-carbethoxy-carbonilamino-2-methyl-6-($\beta$-benzyloxy-ethoxy)-pyrimidine.
8. 4-carbethoxy-carbonilamino-2-methyl-6-methylthio-pyrimidine.
9. 4-carbethoxy-carbonilamino-2-methyl-6-($\beta$-carbethoxy-carboniloxy-ethylthio)-pyrimidine.
10. 4-carbethoxy-carbonilamino-6-chloro-pyrimidine.
11. 4-carbethoxy-carbonilamino-pyrimidine.

TABLE 2

| Symbol | R | $R_1$ | Melting Point °C. | % Yield | PCA Test $ED_{50}$ mg/kg i.p. | $ED_{50}$ mg/kg os | Shay | Antisecretory and antiulcer activity $ED_{50}$ mg/kg os Indometacin | Restraint |
|---|---|---|---|---|---|---|---|---|---|
| 907 | H | $OCH_3$ | 88–9° | 75 | 32 | 100 | 3.2 | 4.6 | 12 |
| 913 | $CH_3$ | $OCH_3$ | 112–13° | 70 | <5 | >100 | 3.6 | 4.2 | 15 |
| 921 | $C_6H_5$ | $OCH_3$ | 107–8° | 75 | 30 | 100 | 6.2 | 15 | 25 |
| 923 | $CH_3$ | $OCH_2CH_2OCH_3$ | 92–4° | 70 | 25 | 70 | 4.1 | 3.2 | 9 |
| 927 | $CH_3$ | $OCH_2CH_2OCH_2$—⟨phenyl⟩ | 67–9° | 66 | 23 | 80 | 6.4 | 14.8 | 16 |
| 928 | $CH_3$ | $SCH_3$ | 113–15° | 73 | 30 | >100 | 7.2 | 2.0 | 14 |
| 929 | $CH_3$ | $SCH_2CH_2OCOCOOC_2H_5$ | 79–80° | 73 | 2.4 | 18 | 8.4 | 22.2 | 18 |
| 931 | H | Cl | 141–3° | 68 | 24 | >100 | 6.3 | 7.2 | 22 |
| 932 | H | $OCH_2CH_2OCH_3$ | 88–9° | 72 | 10 | 26 | 2.1 | 3.2 | 7 |
| 933 | H | H | 120° | 64 | 32 | 96 | 3.8 | 4.7 | 10 |
| 934 | $OCH_3$ | $OCH_3$ | 128–9° | 60 | 25 | >100 | 4.1 | 5.6 | 11 |
| 940 | H | $SCH_2CH_2OCOCOOC_2H_5$ | 81–3° | 61 | 12 | 43 | 5.2 | 3.6 | 8 |
| 953* | H | $SCH_2CH_2CH_2COOC_2H_5$ | 125–8° | 71 | 3.2 | 26 | 7.2 | 8.8 | 12 |
| 955 | $CH_3$ | $SCH_2CH_2OCH_3$ | 73–4° | 67 | 6.9 | 25 | 2.3 | 2.8 | 7 |
| 957 | H | $SCH_2CH_2OCH_3$ | 73–5° | 75 | 5.8 | 23 | 6.2 | 9.4 | 14 |
| 963* | H | $OCH_2CH_2OCH_2CH_2OCH_3$ | 51–3° | 60 | 6.2 | 24 | 6.1 | 7.3 | 16 |
| 965 | H | $SCH_2CH_2OCH_2CH_2OCH_3$ | 98–100° | 61 | 7.3 | 20 | 8.3 | 6.1 | 17 |

*The data shown are related to the hydrochloride.

I claim:

1. Carbethoxy-carbonilamino-pyrimidines having the general formula (I)

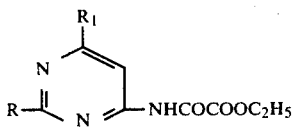

in which
R=H, $CH_3$, $C_6H_5$, $SCH_3$
$R_1$=H, Cl, $OCH_3$, $OCH_2CH_2OCH_3$, $SCH_2CH_2CH_2COOC_2H_5$, $SCH_3$, $SCH_2CH_2OH$, $SCH_2CH_2OCOCOOC_2H_5$, $OCH_2CH_2OCH_2C_6H_5$, $SCH_2CH_2OCH_3$, $SCH_2CH_2OCH_2CH_2OCH_3$.

2. 4-carbethoxy-carbonilamino-6-($\beta$-methoxy-ethoxy)-pyrimidine.

12. 4-carbethoxy-carbonilamino-2,6-dimethoxy-pyrimidine.
13. 4-carbethoxy-carbonilamino-6-($\beta$-carbethoxy-carbonyloxy-ethylthio)-pyrimidine.
14. 4-carbethoxy-carbonilamino-6-($\gamma$-carbethoxy-propylthio)-pyrimidine.
15. 4-carbethoxy-carbonilamino-2-methyl-6-($\beta$-methoxy-ethylthio)-pyrimidine.
16. 4-carbethoxy-carbonilamino-6-($\beta$-methoxy-ethylthio)-pyrimidine.
17. 4-carbethoxy-carbonilamino-6-[$\beta$-($\beta$-methoxy-ethoxy)ethoxy]-pyrimidine.
18. 4-carbethoxy-carbonilamino-6-[$\beta$-($\beta$-methoxy-ethoxy)ethylthio]-pyrimidine.
19. A pharmaceutical composition having an action against allergy and against gastric secretions, characterised by the fact that it contains in the form of active principle one or more compounds in accordance with claim 1.

* * * * *